United States Patent
Aicher

(10) Patent No.: US 10,874,472 B2
(45) Date of Patent: Dec. 29, 2020

(54) STERILE CONTAINER LID WITH OUTER COVER

(71) Applicant: Aesculap AG, Tuttlingen (DE)

(72) Inventor: Gerhard Aicher, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 18 days.

(21) Appl. No.: 16/079,742

(22) PCT Filed: Feb. 21, 2017

(86) PCT No.: PCT/EP2017/053914
§ 371 (c)(1),
(2) Date: Aug. 24, 2018

(87) PCT Pub. No.: WO2017/144454
PCT Pub. Date: Aug. 31, 2017

(65) Prior Publication Data
US 2019/0069970 A1    Mar. 7, 2019

(30) Foreign Application Priority Data

Feb. 26, 2016    (DE) .......................... 10 2016 103 401

(51) Int. Cl.
*A61B 50/30*    (2016.01)
*A61L 2/26*    (2006.01)
*A61B 50/00*    (2016.01)

(52) U.S. Cl.
CPC ................ *A61B 50/30* (2016.02); *A61L 2/26* (2013.01); *A61B 2050/006* (2016.02); *A61L 2202/182* (2013.01)

(58) Field of Classification Search
CPC ..... A61B 50/30; A61B 2050/006; A61L 2/26; A61L 2202/182; A61L 2202/24
(Continued)

(56) References Cited

U.S. PATENT DOCUMENTS 4,372,921 A    2/1983    Sanderson et al.
4,512,498 A    4/1985    Leibinger
(Continued)

FOREIGN PATENT DOCUMENTS

CN    103118711 A    5/2013
CN    104093641 A    10/2014
(Continued)

OTHER PUBLICATIONS

German Search Report for German Application No. 10 2016 103 401.0, dated Oct. 7, 2016, with translation—9 pages.
(Continued)

*Primary Examiner* — J. Gregory Pickett
*Assistant Examiner* — Brijesh V. Patel

(57) ABSTRACT

A lid for a sterile container includes a lid component and at least one gas exchange section on the lid component. The lid also includes at least one frame for receiving a filter device on a lid inner face on the at least one gas exchange section, at least one outer cover which covers the at least one gas exchange section on a lid outer face, and at least one connection element which is inserted in the lid component to secure the outer cover to the lid outer face and secure the frame to the lid inner face. The lid can be incorporated into a sterile container and feature an outer cover.

15 Claims, 3 Drawing Sheets

Figure 1:
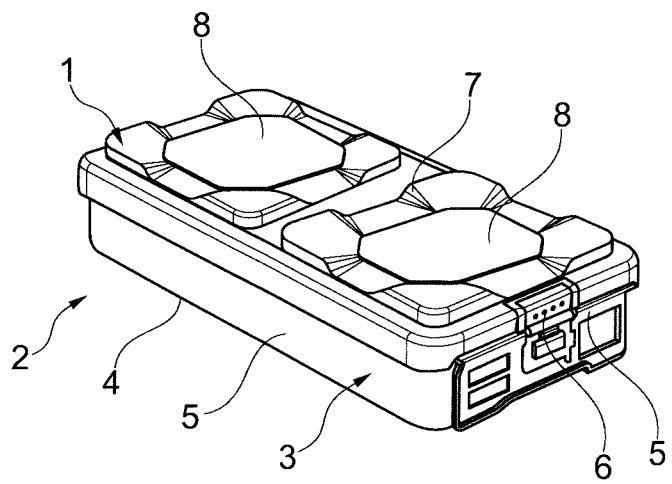

(58) Field of Classification Search
USPC ..... 220/23.87–23.88, 315, 324, 495.01, 784, 220/788, 831–832; 206/439, 807, 1.5
See application file for complete search history.

(56) References Cited

U.S. PATENT DOCUMENTS

| | | | |
|---|---|---|---|
| 4,551,311 A | 11/1985 | Lorenz | |
| 4,661,326 A | 4/1987 | Schainholz | |
| 4,783,321 A * | 11/1988 | Spence | A61L 2/26 422/300 |
| 5,097,865 A * | 3/1992 | Riley | A61L 2/26 137/529 |
| 5,176,884 A | 1/1993 | Taschner et al. | |
| 5,346,075 A | 9/1994 | Nichols et al. | |
| 5,524,755 A | 6/1996 | Deeds | |
| 5,690,713 A | 11/1997 | Bowerman et al. | |
| 6,053,914 A | 4/2000 | Eggers et al. | |
| 6,077,485 A * | 6/2000 | Baker | A61L 2/26 206/363 |
| 6,145,687 A | 11/2000 | Nichols et al. | |
| 6,620,390 B1 * | 9/2003 | Wagner | A61L 2/26 206/325 |
| 6,622,862 B1 * | 9/2003 | Corrado | A61L 2/07 206/363 |
| 7,132,089 B2 * | 11/2006 | Lacabanne | A61L 2/24 422/292 |
| 7,381,385 B2 | 6/2008 | Gleichauf et al. | |
| 7,914,751 B2 * | 3/2011 | Oertmann | A61L 2/26 422/292 |
| 2002/0136679 A1 * | 9/2002 | Frieze | A61L 2/26 422/300 |
| 2004/0256269 A1 | 12/2004 | Gleichauf et al. | |
| 2005/0004551 A1 | 1/2005 | Barrelle | |
| 2006/0076081 A1 | 4/2006 | Gleichauf et al. | |
| 2007/0084862 A1 * | 4/2007 | Jakab | A61L 2/022 220/4.01 |
| 2013/0175276 A1 | 7/2013 | Gleichauf et al. | |
| 2014/0079589 A1 * | 3/2014 | Landgrebe | A61L 2/20 422/28 |
| 2015/0053703 A1 | 2/2015 | Kreidler et al. | |
| 2015/0114923 A1 | 4/2015 | Horz | |
| 2017/0239381 A1 * | 8/2017 | Cohen | A61L 2/26 |

FOREIGN PATENT DOCUMENTS

| | | |
|---|---|---|
| DE | 8213351 U1 | 10/1982 |
| DE | 3500026 A1 | 7/1986 |
| DE | 10156937 A1 | 6/2003 |
| DE | 10210905 A1 | 7/2003 |
| DE | 102008053301 A1 | 4/2010 |
| DE | 102010037659 A1 | 3/2012 |
| DE | 203096079 U | 9/2013 |
| DE | 202013007581 U1 | 9/2013 |
| WO | 03041604 A1 | 5/2003 |

OTHER PUBLICATIONS

International Search Report and Written Opinion for International Application No. PCT/EP2017/053914, dated Jun. 20, 2017—7 pages.

Entire patent prosecution history of U.S. Appl. No. 10/845,780, filed May 13, 2004, entitled, "Sterile Container," now U.S. Pat. No. 7,172,740, issued Feb. 6, 2007.

Chinese Search Report received in Application No. 2017800135388 dated Aug. 13, 2020, 6 pages.

First Chinese Office Action received in Application No. 201780013538.8 dated Aug. 19, 2020, 10 pages.

* cited by examiner

STERILE CONTAINER LID WITH OUTER COVER

RELATED APPLICATIONS

This application is the United. States national phase entry of International Application No. PCT/EP2017/053914, filed Feb. 21, 2017, which claims the benefit of priority of German Application No. 10 2016 103 401.0, filed Feb. 26, 2016. The contents of International Application No. PCT/EP2017/05391.4 and German Application No. 10 2016 103 401.0 are incorporated by reference herein in their entireties.

FIELD

The disclosure relates to a lid for a sterile container comprising a lid component on which at least one gas exchange section, in particular a perforated gas exchange section, is provided, at least one frame for receiving a filter device which is provided on a lid inner face on the at least one gas exchange section, and at least one outer cover which covers the at least one gas exchange section on a lid outer face.

Furthermore, the disclosure relates to a sterile container comprising such a lid, as well as to an outer cover for a sterile container lid for covering at least one, in particular perforated gas exchange section provided in a lid component on the lid outer face.

BACKGROUND

Clinical instruments, objects or the like which come into contact with wounds or open parts of the body, for example, must be sterile or undergo sterilization before being used on humans. This means ensuring the complete absence of bacteria, fungi, viruses and spores or killing all microorganisms with the aim of achieving absolute sterility of the corresponding instruments and objects. The instruments and objects are placed in a sterile container in which sterilization is carried out.

Steam sterilization, also known as wet heat sterilization, is used as the sterilization process, in which a vacuum is first generated in a sterile container in a de-aeration phase and then steam with high heat and high pressure enters the sterile container in a sterilization phase, thereby destroying microorganisms located on the objects to be sterilized. In addition, chemical sterilization processes and radiation-based sterilization are also used.

In prior art, a lid for a sterile container, a sterile container and an outer cover for a sterile container lid are known. This is a plastic lid with an integrated, permanent germ retention system which is validated for 5,000 sterilization cycles. It comprises a lid component made of plastic, in particular polyarylsulfone (PPSU), which has injection-molded pins on the lid inner face, to which a frame for receiving a filter device can be attached by means of ultrasonic welding.

An outer cover made of plastic, in particular polyarylsulfone, covers the perforated gas exchange section to protect the filter device from mechanical influences, for example during transport or storage. In the known sterile container lid, the outer cover is attached to the lid component using clamps provided on the former by means of injection-molding.

However, the prior art sterile container lid has shown that even polyarylsulfone (PPSU), as a high-temperature and high-performance plastic, is very susceptible to aging, especially after more than 5,000 sterilization cycles. It has turned out that plastics as material for sterile container lids are attacked by the temperature and pressure conditions in steam sterilization or by chemical substances in chemical sterilization processes and that this results in gradual aging, which is associated with the release of plasticizers and cracking in the sterile container lid or in the outer cover.

In addition, it has been found that an outer cover made of plastic, in particular polyarylsulfone, is no longer sufficiently shock-proof and scratch-resistant as it ages and does not provide adequate protection against mechanical influences.

For these reasons, the aim is to replace the plastic lid from prior art with a metal lid that is less susceptible to aging and thus more resistant to the process conditions during sterilization. However, the problem has arisen that the connection concept or the attachment of the parts attached to the lid component such as the frame and the outer cover cannot be transferred from a plastic lid to a metal lid. In particular, the freedom of design in the injection moulding process allows the plastic lids or covers to be provided with molded pins or clamps as desired, which can be used to produce the connection of the individual parts to each other.

The prior art has thus the disadvantage that plastics as materials for sterile container lids are susceptible to aging, particularly due to the process conditions during sterilization, and are therefore susceptible to cracking, and the connection concept used in the plastic lid cannot be transferred to other materials, especially not to metals.

SUMMARY

To avoid or overcome the disadvantages arising from prior art, a suitable metal outer cover and a connection concept for attaching or fastening the frame and the outer cover to a metal lid component shall be provided. In particular, the fastening of the outer cover and the frame to the lid component should be easy to achieve and the number of connection elements used should be kept to a minimum. In addition, the outer cover should be easy to manufacture and easy to assemble on the lid component.

According to the disclosure, a lid is provided for a sterile container, comprising a lid component, in particular made of metal, on which at least one gas exchange section, in particular perforated gas exchange section, is provided, at least one frame for receiving a filter device which is provided on a lid inner face on the at least one gas exchange section, at least one outer cover, in particular made of metal, which covers the at least one gas exchange section on a lid outer face, and further comprising at least one connection element/connecting part which is inserted in/attached to the lid component and via which the outer cover can be fastened to the lid outer face and the frame can be fastened to the lid inner face.

Thus, both the outer cover for protecting the filter device and covering the gas exchange section as well as the frame for receiving the filter device are fastened by means of a connection element or connecting part/component inserted in/attached to/integrated in the lid component, so that two connections, namely a connection on the lid inner face/side and a connection on the lid outer face/side, can be made by means of one connection element. This makes it possible to keep the number of connection elements at a low level and, even with metal components, to ensure a suitable attachment of the frame and the outer cover to the lid component via the connection element/part entering two connections.

It is advisable if the connection element is a bolt-like connection element and has a fastening section to which the connection element is non-positively attached to the lid component, in particular by a press-fit.

In this way, a force-fitting or friction-locking, i.e. backlash-free, firm connection is established between the fastening section of the bolt-like connection element and the lid component, preferably by pressing the connection element into a bore of the lid component. In particular, the fastening section of the connection element and the bore of the lid component form an oversize fit or press fit. The bolt-like connection element, in particular a bolt, may have a stop on the fastening section, via which the pressing distance can be limited in the axial direction. Furthermore, the connection element can be fastened or attached to the lid component from both the lid inner face and the lid outer face. The connection between the lid component and the connection element is thus easy to establish and no additional fastening means such as screws, rivets, etc. are required for fastening the connection element to the lid component, which is why no separate fastening means are visible on the lid outer face or lid inner face. This enables a suitable fastening of the connection element to the lid component.

It is also advantageous if the preferably bolt-like connection element, which is preferably a bolt, projects or protrudes inwards toward the lid inner side and outwards toward the lid outer side and forms an internal, first connecting section/inner connecting section and an external, second connecting section/outer connecting section.

The connection element advantageously is a bolt and designed in the manner of a double bolt. The internal, first connecting section of the connection element is provided for fixing or attaching the frame and the external, second connecting section is provided for fixing or attaching the outer cover. Both connecting sections may have a limitation or restriction of the axial insertion of the bolt into the outer cover or into the frame, in particular in the form of a stop or an increase in diameter. In other words, the connection element can therefore comprise pin-like and flange-like sections. This ensures a defined position between the outer cover and the lid component as well as between the frame and the lid component. The general advantage of forming an inner connecting section and an outer connecting section is that two components can be fastened to the lid component with one connection element, in particular with a bolt, which are preferably also positioned relative to one another and relative to the lid component. It is thus possible to fasten two components, namely the frame and the outer cover, to the connection element and thus to the lid component in a torque-proof and immovable manner.

An advantageous exemplary embodiment is characterized in that the outer cover on the outer cover inner face has at least one receptacle for a force-locking and/or form-fitting reception, in particular by clamping, snapping or clipping, of the external, second connecting section/outer connecting section of the bolt-like connection element, in particular the bolt.

According to the disclosure, the outer cover can be placed/pushed/inserted/clipped/locked/clamped on/into/onto the protruding/projecting bolt-like connection element, so that a non-positive and/or positive connection is created between the bolt/the bolt-like connection element/the external, second connecting section of the bolt-like connection element and the outer cover.

In accordance with the disclosure, a spring clamping disc is preferably provided for the force-locking reception of the outer connecting section of the bolt-like connection element. This allows a secure connection between the outer cover and the lid component to be established, in particular by inserting a protruding bolt into a spring clamping disc provided on the outer cover inner face and clamping it.

Due to the fact that the receptacle is provided on the outer cover inner face, the bolt or connection element is not visible from the lid outer side. This has the advantage that there is no externally visible connection between the lid component and the outer cover, as is often the case with screw connections, for example. Furthermore, it is possible to provide a smooth outer surface where no moisture accumulation occurs.

In accordance with the disclosure, it is thus possible to provide an invisible, simple, permanent and durable connection between the outer cover and the lid component, which can preferably be produced with just one click.

In combination, the outer cover inner face and the outer cover outer face form the outer cover according to the disclosure, the outer cover according to the disclosure being preferably an integral, one-piece and/or one-material component. However, it is also conceivable according to the disclosure to provide a separate clamping component on the outer cover inner face, which is attached to the outer cover, in particular in a material-bonding manner.

Furthermore, it is advisable if the frame can be fixed to the internal, first connecting section/the inner connecting section of the bolt-like connection element in a force-locking manner, in particular by pressing, or in form-fitting manner, in particular by clipping or snapping it in place.

Preferably, the frame is pressed, clipped or snapped in place, which creates a torque-proof and immovable connection between the frame and the connection element. Thus, a secure, simple, permanent and/or durable connection between the frame and the bolt-like connection element/bolt can be established via the inner connecting section.

In an advantageous embodiment, the filter device accommodated in the frame has a holder and a filter element and the filter device is covered on the lid inner face by an inner cover, with the holder and/or the filter element and/or the inner cover being attachable to the inner connecting section of the bolt-like connection element.

It is thus provided in accordance with the disclosure that, in addition to the frame, also the holder and/or the filter element, which is preferably a filter membrane made of polytetrafluoroethylene (PTFE), and/or the inner cover can be fastened to the internal, first connecting section of the bolt-like connection element. This has the advantage that not only two, but three, four or even five components, namely the outer cover, the frame, the holder, the filter element and the inner cover, can be attached to the lid component via one connection element. This makes it possible to further reduce the number of required fastening means, such as screws, rivets, welding spots, etc.

The lid component is advantageously made of a light metal, preferably aluminum, which is in particular resistant to sterilization, and/or the outer cover is made of metal, in particular a sterilization-resistant and/or wear-resistant and/or highly rigid and/or high-strength metal, preferably stainless steel, in particular in the manner of a sheet metal/steel sheet.

The use of a light metal, especially aluminum, has the advantage that a sterilization-resistant and age-resistant material is used for the lid component, which does not increase the mass of the sterile container excessively as compared to a plastic lid. In addition, the use of a light metal as a lid component greatly increases the mechanical properties of the lid compared to plastic, so that the lid is better protected against external mechanical influences.

The use of a metal, preferably stainless steel, for the outer cover has the advantage that an extremely impact-resistant, dimensionally stable, scratch-resistant, sterilization-resistant and age-resistant material is used. If the metal is of the sheet metal type, a simple and cost-effective production of the cover is also guaranteed, for example by a cutting process, in particular laser cutting, water jet cutting, flame cutting, or by punching with subsequent suitable forming or welding. In addition, the sterile container lid can be easily given a higher quality appearance/exterior appearance/design by using aluminum for the lid component and stainless steel for the outer cover.

In an advantageous embodiment, at least two, preferably three, four, five or more, further preferred four receptacles are provided on the outer cover inner face for receiving the outer connecting section of the bolt-like connection element, which are uniformly distributed, in particular equally distributed over the outer cover inner face.

The number of connection elements corresponds to the number of receptacles on the outer cover inner face, so that an external, second connecting section of a bolt-like connection element/bolt is received in each dedicated receptacle. This also means that the same number of internal, first connection sections is provided on the lid inner face. The even distribution of the receptacles on the outer cover inner face and thus the even distribution of the bolt-like connection elements, preferably around the circumference of the gas exchange section, ensures a uniform and thus no one-sided or punctual transmission or introduction of forces between the lid component/the bolt-like connection element and the outer cover on the one side and the frame on the other side. This has the advantage that both the frame and the outer cover can be fixed or fastened easily and securely.

The present disclosure also relates to a sterile container with a receiving container comprising a container bottom and container walls and with a lid described above for closing the sterile container.

Furthermore, the present disclosure relates to an outer cover for a sterile container lid, in particular for a lid as described above or a lid, for covering at least one gas exchange section provided in a lid component on a lid outer face, which has at least one receptacle on an outer cover inner face for positive and/or non-positive gripping, in particular clamping, snapping or clipping a bolt-like connection element, preferably a bolt.

This means that the bolt-like connection element, preferably the bolt, that projects outwards from the lid component, is received on the outer cover inner face and can be fastened in an easy manner. This allows the connection element to be invisible on the outer cover outer face. Preferably the fastening is done by clamping, snapping or clipping, so that for the fastening of the outer cover to the lid component it is only necessary to insert or place the at least one receptacle of the outer cover in/on the at least one bolt-like connection element. This allows an extremely simple installation of the outer cover on the lid component.

In an advantageous embodiment, the receptacle is provided on a projection on which a clamping device, in particular a spring clamping disc, is formed for clamping the bolt-like connection element, and/or the clamping device can be transferred to a state of engagement by inserting the bolt-like connection element.

The projection is preferably designed in such a way that under the clamping device or toward the outer cover outer face there is a cavity or a receiving space for the bolt-like connection element or bolt into which the bolt can be inserted. The projection is formed such that the length of the protruding section is greater than or equal to the length of the outer connecting section of the bolt.

If the bolt is inserted into the clamping device, in particular into the spring clamping disc, the spring clamping disc changes from a normal, relaxed state into a state bent outward or toward the outer cover outer face in which it exerts a spring force on the inserted bolt and fixes it frictionally or non-positively, so that slipping out or axial movement of bolt or outer cover is prevented. Preferably, the outer cover can only be removed again by applying a great deal of force. This ensures easy insertion and secure fastening while at the same time preventing slipping out. Thus, the core idea of the present disclosure, i.e. to fix the outer cover to the lid component in a simple manner, can be guaranteed. In addition to the spring force, the bolt can also snap into place or be positively locked in the outer cover.

It is useful if the outer cover is made from a sheet metal part and the projection is formed by forming and/or by unfolding at least one outer cover corner section and/or the clamping device, in particular the spring clamping disc, is formed on the projection by providing a recess, in particular by punching.

The advantage of producing the outer cover from a sheet metal part is that it can be produced simply, cost-effectively and quickly by punching or by a cutting process. The same applies to the formation of the projection by forming an outer cover corner section and the formation of the spring clamping disc by providing a suitable recess already before forming. Thus, the entire production of the outer cover can be realized quickly, easily and cost-effectively.

In an advantageous manner, the folded outer cover corner section is bent over at least three times and has at least a first, a second and a third bending edge, and a middle section which is substantially parallel to the outer cover outer face is formed between the second and the third bending edge and comprises the clamping device, and/or an end section is fastened to the outer cover after the third bending edge, preferably in a material-bonding manner.

In particular the fastening of an end section of the outer cover corner section to the outer cover, preferably in a material-bonding manner by welding, has the advantage that the projection is rigid and stable and the connection is not visible on the outer cover outer face. If a middle section parallel to the outer cover outer face is also provided with the clamping device, simple insertion of a bolt is guaranteed.

In an advantageous embodiment, a separate clamping component is fastened to the outer cover inner face, in particular in a material-bonding manner, which has the receptacle for a bolt-like connection element, in particular for a bolt.

In accordance with the disclosure, a clamping component separate from the outer cover can thus also be provided, which is attached to the outer cover inner face in a material-bonding manner. This has the advantage that a greater freedom of design of the projection is guaranteed compared to a bent corner section.

In other words, the disclosure relates to a double bolt as a connection element and an external cover/outer cover made of sheet steel for the container lid/sterile container lid PrimeLine made of aluminum, whereby the connection between the container lid and the cover is invisible.

Therefore no screws, rivets, etc. are used to connect the cover to the sterile container lid. The aim is to provide a high-quality, nice, stable, cost-effective and easy-to-install metal cover.

According to the disclosure, a spring clamping disc provided on the cover is simply snapped in place on a protruding/projecting bolt pressed into the sterile container lid, thus enabling a secure connection between the cover and the aluminum lid. This bolt also protrudes inwards and holds the frame for a filter on the lid inner side.

On the one hand, this provides an invisible, simple and durable connection between the cover and the lid; on the other hand, at least two connections can be made with a bolt or press-fit bolt, which protrudes both inwards and outwards.

This double bolt allows bath the cover, which consists of one part, and the frame to be attached to the lid. The cover can preferably be mounted/latched on the lid with one click and covers the filter surface of the container lid. According to the disclosure, four double bolts are preferably provided, so that both the inner frame/frame and the cover can be fastened/fixed in a simple manner.

BRIEF DESCRIPTION OF THE DRAWING FIGURES

The disclosure is further explained with the help of the following Figures, which are only schematic in nature and serve exclusively for the understanding of the disclosure. The same elements are provided with the same reference symbols. The features of the individual exemplary embodiments can be interchanged.

Figure 2:
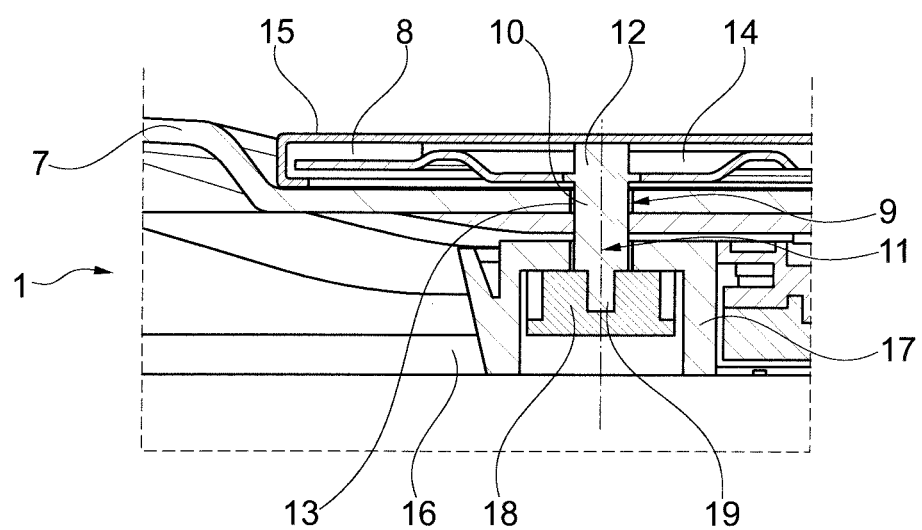
Figure 3:
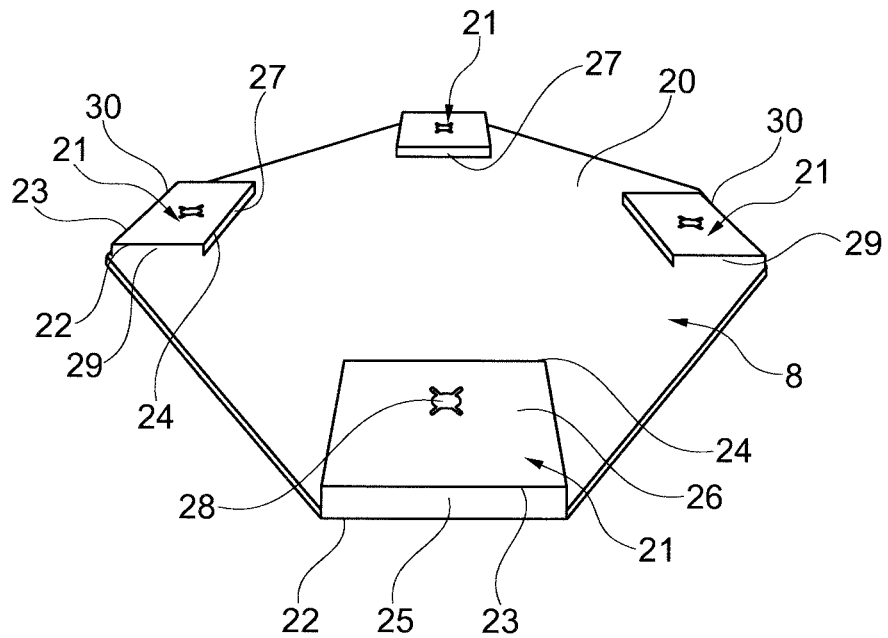
Figure 4:
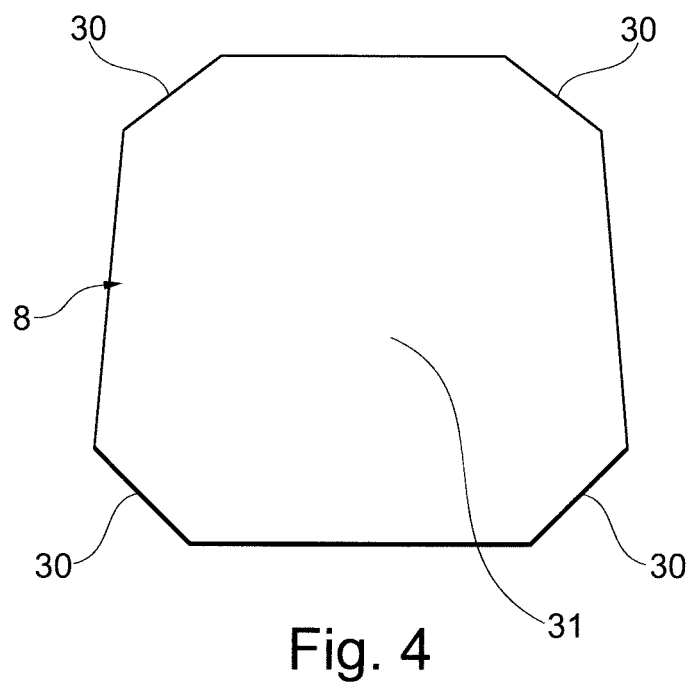
Figure 5:
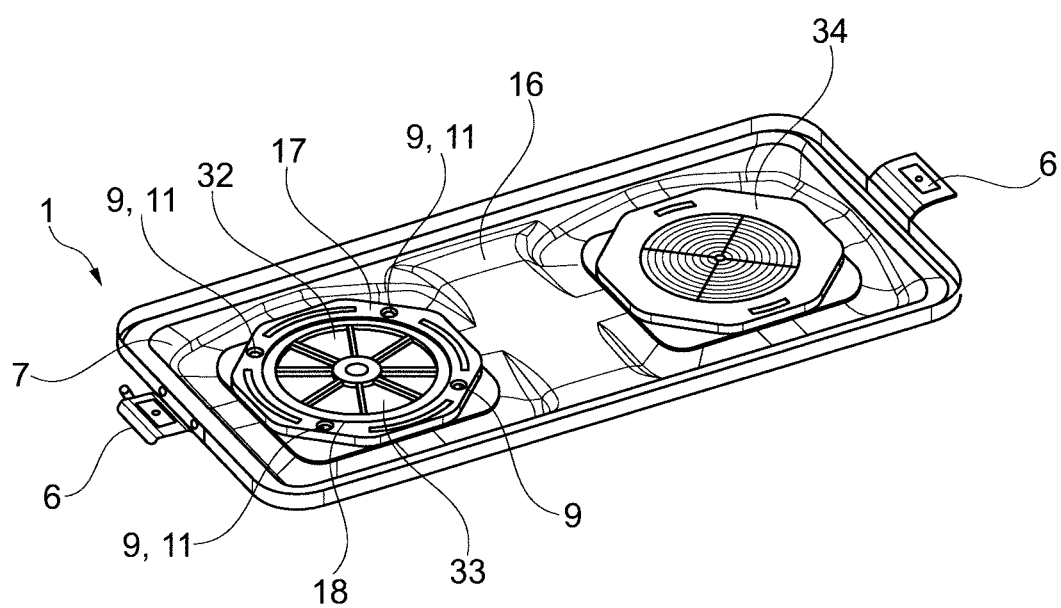

FIG. 1 is a perspective view of a sterile container according to the disclosure with lid and receiving container, FIG. 2 is a sectional view of the lid according to the disclosure, which shows a bolt pressed in a lid component, to which bolt the lid according to the disclosure is fastened on one side and to which a frame is fastened on the other side, FIG. 3 is a perspective view of the inner face of the outer cover according to the disclosure, FIG. 4 is a perspective view of the outer face of the outer cover according to the disclosure, and FIG. 5 is a perspective view of the inner face of the lid according to the disclosure.

DETAILED DESCRIPTION

FIG. 1 shows an isometric view of a lid 1 according to the disclosure for a sterile container 2, which closes a receiving container 3. The receiving container 3 consists of a container bottom 4 and container walls 5 extending upward from said container bottom. A closure 6 closes the receiving container 3 and the lid 1. The lid 1 has a lid component 7 which is made of aluminum and covered on the outside by two outer covers 8 made of sheet steel. Under the outer covers 8, perforated sections or sections in the form of hole plates (not shown) are provided on the lid component 7. No screws, rivets or similar are visible from the outside which attach the outer covers 8 to the lid component 7.

FIG. 2 shows a sectional view of the lid 1 according to the disclosure, which shows a bolt/connection element 9 pressed into the lid component 7. The bolt 9 has a fastening section 10, an inner connecting section 11 and an outer connecting section 12. The fastening section 10 of the bolt 9 is pressed into a hole 13 of the lid component 7. The hole 13 and the fastening section 10 thus form a press fit. The bolt 9 has a flange 14, which limits the axial insertion or press-in amount of the bolt 9 from the lid outer face 15 at the lid component 7. The flange 14 thus forms a stop on the lid component 7. The outer cover 8 is fastened to the outer connecting section 12 of the bolt 9. The flange 14 also forms a stop for the outer cover 8. On the lid inner face 16, both a frame 17 and another component, for example a filter holder 18, are attached to the inner connecting section 11 of the bolt. First, the frame 17 is pressed onto the inner connecting section 11 of the bolt 9 and then the other component, for example the filter holder 18, is fitted onto a pin 19 of the inner connecting section 11. Thus, both the frame 17 and the filter holder 18 are fastened to the inner connecting section 11.

FIG. 3 shows an isometric view of the inner face or outer cover inner face 20 of the outer cover 8 according to the disclosure. Four projections 21 are provided on the outer cover inner face 20. The projections 21 each consist of a first bending edge 22, a second bending edge 23 and a third bending edge 24, or of a start section 25 between the first bending edge 22 and the second bending edge 23, a middle section 26 between the second bending edge 23 and the third bending edge 24, and an end section 27 following the third bending edge 24. A receptacle/spring clamping disc/recess/clamping device 28 is provided in the center of each middle section 26. The start section 25, the middle section 26 and the end section 27 or the first bending edge 22, the second bending edge 23 and the third bending edge 24 are produced by forming the outer cover 8, which is a sheet metal 110 part. The end sections 27 are fastened to the outer cover 8 by welding. A cavity 29 is surrounded by the start section 25, the middle section 26 and the end section 27, in which cavity an outer connecting section 12 of a bolt 9, which is inserted in the spring clamping disc/receptacle/recess/clamping device 28, can be received. The projections 21 in FIG. 3 are each provided at outer cover corner sections 30. The projections 21 are formed in one piece from one material and are integral is with the outer cover 8.

FIG. 4 shows an isometric view of the outer cover outer face 31 of the outer cover 8 according to the disclosure. The outer cover outer face 31 represents a smooth, flat surface. No connection elements are visible from the outer cover outer face 31. The outer cover corner sections 30 are formed so as to be retracted. Due to the retracted outer cover corner sections 30, the outer cover 8 has an octagonal shape.

FIG. 5 shows an isometric view of a lid inner face 16 of the lid 1 according to the disclosure. The frame 17, in which a filter device 32 is accommodated, is provided on the left side of the lid component 7 on the lid inner face 16. The filter device 32 consists of the filter holder 18 and the filter element/filter membrane 32. The frame 17 is fixed to the lid component 7 at four inner connecting sections 11 of the bolts 9. On the right in FIG. 5, the arrangement shown on the left is illustrated covered by an inner cover 34.

The invention claimed is:

1. A sterile container comprising:
   A) a receiving container having a container bottom and container walls,
   B) a lid for closing the receiving container,
   C) at least one outer cover for the lid; and
   D) at least one connection element,
   the lid comprising:
      a lid component which is provided with at least one gas exchange section; and
      at least one frame provided on a lid inner side on the at least one gas exchange section,
   wherein the at least one outer cover covers the at least one gas exchange section of the lid component on a lid outer side,
   wherein the at least one connection element is inserted in the lid component,
   wherein the at least one connection element fastens the at least one outer cover on the lid outer side,
   wherein the at least one connection element fastens the at least one frame on the lid inner side; and wherein the outer cover comprises at least one receptacle on an outer cover inner face for force-locking or form-fitting reception of the at least one connection element.

2. The sterile container according to claim 1, wherein the at least one connection element is a bolt-like connection element and has a fastening section at which the at least one connection element is fastened in a force-locking manner to the lid component.

3. The sterile container according to claim 2, wherein the at least one connection element projects inwardly towards the lid inner side and outwardly towards the lid outer side and forms an inner first connecting portion and an outer second connecting portion.

4. The sterile container according to claim 3, wherein the at least one outer cover has at least one receptacle for force-locking or form-fitting reception of the outer second connecting portion of the bolt-like connection element on an inner side of the at least one outer cover.

5. The sterile container according to claim 4, wherein the at least one frame is fastened to the inner first connecting portion of the bolt-like connection element in a force-locking manner or in a form-fitting manner.

6. The sterile container according to claim 3, further comprising a filter device received in the at least one frame, the filter device having a holder and a filter element and being covered by an inner cover from the lid inner side, the holder or the filter element or the inner cover being attachable to the inner first connecting portion of the bolt-like connection element.

7. The sterile container according to claim 3, wherein the at least one frame is fastened to the inner first connecting portion of the bolt-like connection element in a force-locking manner or in a form-fitting manner.

8. The sterile container according to claim 1, wherein the lid component is made of a light metal.

9. The sterile container according to claim 8, wherein the at least one outer cover is made of a metal.

10. The sterile container according to claim 1, wherein the at least one outer cover is made of a metal.

11. The sterile container according to claim 1, wherein the at least one connection element is a bolt-like connection element.

12. An outer cover for a sterile container lid for covering at least one gas exchange section provided in a lid component on a lid outer side, the outer cover comprising at least one receptacle on an outer cover inner face for force-locking or form-fitting reception of a bolt-like connection element, and wherein the at least one receptable is provided on a projection on which a clamping device is formed for clamping the bolt-like connection element.

13. The outer cover according to claim 12, wherein the outer cover is manufactured from a sheet metal part and the projection is formed by at least one of forming and unfolding at least one outer cover corner portion.

14. The outer cover according to claim 12, wherein the clamping device is transferred into a state of engagement by inserting the bolt-like connection element.

15. The outer cover according to claim 12, wherein the clamping device is formed on the projection by providing a recess.

* * * * *